United States Patent [19]
Harding et al.

[11] Patent Number: 5,932,246
[45] Date of Patent: Aug. 3, 1999

[54] THERAPEUTIC USES OF VERAPAMIL ENANTIOMERS

[75] Inventors: Deborah Phyllis Harding; Jane Lizbeth Greaves, both of Cambridge, United Kingdom

[73] Assignee: Darwin Discovery Limited, United Kingdom

[21] Appl. No.: 08/907,151

[22] Filed: Aug. 6, 1997

[30]   Foreign Application Priority Data

Aug. 6, 1996 [GB] United Kingdom .................... 9616504

[51] Int. Cl.$^6$ ................................ A61K 9/20; A61K 9/48
[52] U.S. Cl. ........................ 424/451; 424/456; 424/457; 424/464; 424/468; 514/646; 514/821
[58] Field of Search ..................... 424/456, 464, 424/489, 451, 457, 468; 514/646, 821

[56]            References Cited

U.S. PATENT DOCUMENTS 5,057,304  10/1991  Kretzschmar et al. .................... 424/10
5,733,756   3/1998  Zeitlin et al. ........................... 435/122

FOREIGN PATENT DOCUMENTS 9509150   4/1995  WIPO .

OTHER PUBLICATIONS

Van Meel, J.C.A., et al. (1983) "Differential inhibition of $\alpha_2$–adrenoceptor–mediated pressor responses by (+)–and (−)–verapamil in pithed rats" Journal Pharm. Pharmacol. 35:500–504.

Longstreth, James A., "Verapamil: A Chiral Challenge to the Pharmacokinetic and Pharmacodynamic Assessment of Bioavailability and Bioequivalence" (1983).

Raschack, M., and K. Engelmann (1983) "Calcium Antagonistic Activity and Myocardial Ischemic Protection by Both Stereoisomers of Verapamil" Adv. Miocardiol. vol. 4, pp. 505–512.

Chiba, S. et al. (1978) "Effects of Optical Isomers of Verapamil on SA Nodal Pacemaker Activity and Contractility of the Isolated Dog Heart" Jpn. Heart J. 19(3):409–414.

Rabkin, S.W. (1994) "Verapamil Has Antiarryhthmic Effects That are mediated in Brain Through Endogenous Opioids" J. Cardiovac. Pharmacol. 23(5):814–821.

Thandroyen, F.T., et al. (1986) "The Influence of Verapamil and its Isomers on Vulnerability to Ventricular Fibrillation During Acute Myocardial Ischemia and Adrenergic Stimulation in Isolated Rat Heart" J. Mol. Cell. Cardiol. vol. 18, pp. 645–649.

Raschack, M. (1976) "Relationship of Antiarrhythmic to Inotropic Actibity and Antiarrhythimic Qualities of the Optical Isomers of Verapamil" Nauyn–Schmiedeberg's Arch. Pharmacol. 294, 285–291.

Curtis, M.J., M.J.A. Walker (1986) "The Calcium Antagonist Potency Ratio of the Optical Enantiomers of Verapamil in a Variety of Preparations" Proc. West. Pharmacol. Soc. 29:295–297.

Curtis, M.J., M.J.A. Walker (1986) "The Mechanism of Action of the Optical Enantiomers of Verapamil Against Ischaemis–Induced Arrhythimias in the Conscious Rat" Br. J. Pharmac. 89, 137–147.

Berkow, R., and A.J. Fletcher (eds.) (1992) "Diseases of the Heart and Pericardium" in The Merck Manual of Diagnosis and Therapy, $16^{th}$ edition, published by Merck Research Laboratories, pp. 474–477.

Nayler, W. G. and W.J. Sturrock (1983) "An Inhibitory Effect of Verapamil and Diltiazem on the Resease of Noradrenaline from Ischaemic and Reperfused Hearts" J. Mol. Cell. Cardiol. 16:331–344.

Arita, Makoto, and Tatsuto Kiyosue (1983) Modification of " Depressed Fast channel Dependent Slow Conduction" by Lidocaine and Verapamil in the Presence of Absence of Catecholamines Evidence for Alteration of Preferential Ionic Channels for Slow Conduction Japanese Circulation Journal 47:68–80.

Arita, Makoto, et al. (1983) "Nature of Residual Fast Channels" Dependent Action Potentials and Slow Conduction in Guinea Pig Ventricular Muscle and Its Modification by Isoproterenol" The American Journal of Cardiology, 51:1433–1440.

Watanabe, Hidehiko, et al. (1981) "Effects of Imipramine on Frequency–Force Relationship in Isolated Right Atrial Muscle of the Dog" Japan. J. Pharmacol. 31:289–291.

Surakitbanharn, Yosyong, et al. (1995) "Self–Association of Dexverapamil in Aqueous Solution" Journal of Pharmaceutical Sciences, 84(6):720–723.

Motzer, Robert, et al. (1995) "Phase I/II Trial of Dexverapamil Plus Vinblastine for Patients with Advanced Renal Cell Carcinoma" Journal of Oncology, 13(8):1958–1965.

Satoh, Keisuke, et al. (1980) "Coronary Vasodilator and Cardiac Effects of Optical Isomers of Verapamil in the Dog" Journal of Cardiovascular Pharmacology 2:309–318.

Simamora, et al. (1994) "Compatibility Studies of Intravenous Dexverapamil Formulations" Pharmaceutical Research, 11(10):S277 abstract.

*Primary Examiner*—Thurman K. Page
*Assistant Examiner*—James M. Spear
*Attorney, Agent, or Firm*—Saliwanchik, Lloyd & Saliwanchik

[57]            ABSTRACT

Substantially single enantiomer (R or S) verapamil, or a pharmaceutically-acceptable salt thereof provides an improved treatment for patients having a condition susceptible to treatment with racemic verapamil and who are disposed to constipation.

7 Claims, No Drawings

THERAPEUTIC USES OF VERAPAMIL ENANTIOMERS

FIELD OF THE INVENTION

This invention relates to improved treatment of patients having conditions which are susceptible to treatment with racemic verapamil, but who are disposed to constipation as a side effect thereof.

BACKGROUND OF THE INVENTION

Verapamil (1) is presently in clinical use as a racematic for the treatment of hypertension, angina, atrial fibrillation and paroxysmal supraventricular tachycardia. However, constipation is a well known and undesirable side effect of this drug with a reported incidence up to 38% of all patients treated; see C. Yedinak, American Pharmacy (1993) NS 33:8; 49–66. This can result in reduced compliance or even cessation of treatment.

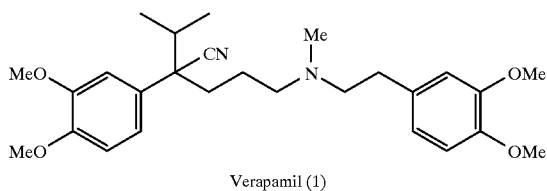

Verapamil (1)

The opposite enantiomers of verapamil have different biological activities and different potencies. The pharmacological profile is determined by stereoselectivity of pharmacodynamics and pharmacokinetics.

The (R)-enantiomer may be of benefit for the reversal of multi-drug resistance in cancer chemotherapy (see Eliason, Int. J. Cancer (1990) 46: 113).

The (S)-enantiomer may be of benefit in the treatment of atrial fibrillation (see Raschack, Naunyn-Schmiedeburg's Arch Pharmacol. (1976)294: 285–297). It may also be of benefit in the treatment of angina (see Curtis et al., Br. J. Phamac. (1986)89: 137–147), although dose-limiting side effects are reported to be associated with its use, such as depression in myocardial activity (see Satoh et al, Journal of Cardiovascular Pharmacology (1980)2: 309–318) and atrioventricular (AV) conduction block (see Raschack, as above).

SUMMARY OF THE INVENTION

Surprisingly, it has now been found that administration of either of the individual enantiomers (R or S) of verapamil, at a dosage less than the standard treatment dosage of verapamil racemate, eg. 360 mg per day, does not delay large bowel transit, thereby removing the risk of constipation often experienced on treatment with the racemate. It may, therefore, prove beneficial to administer a substantially single enantiomer of verapamil for the treatment of a condition susceptible to treatment by the racemate, and for which the respective enantiomer has the majority of the therapeutic activity for treatment of that condition, thereby allowing a reduction in dosage compared with the racemate, in patients disposed to constipation.

DESCRIPTION OF THE INVENTION

For the purposes of the present invention, by a patient disposed to constipation typically we mean a patient who suffers from a difficult or infrequent passage of faeces after treatment with a standard treatment dosage, eg. 360 mg per day, of verapamil racemate; a patient whose colon does not respond to the usual stimuli providing evacuation of the colon; or a patient in whom accessory stimuli normally provided by eating or physical exercise are lacking, eg. a bedridden patient. The use of drugs for medical conditions usually associated with constipation frequently compounds the problem, eg. opiates and anti-depressants. In addition, patients suffering from neurological diseases, such as Parkinson's disease, frequently suffer from constipation..

Furthermore, by substantially single enantiomer typically we mean that the desired enantiomer is in an enantiomeric excess of at least 70% by weight as compared to the other enantiomer, preferably at least 95%, or higher. The enantiomer may be enantiopure. It may be used in the form of any suitable salt, eg. the hydrochloride.

The utility of the present invention lies in the treatment of any condition susceptible to treatment by verapamil racemate. Patients for which it may have particular utility include those who are cardiac-compromised, and therefore ill-equipped to cope with strain that may result from constipation. By cardiac-compromised typically we mean a patient suffering from any form of heart disease, and in particular from any of the following conditions: atrial fibrillation, angina, hypertension, and paroxysmal supraventricular tachycardia. It may also have utility in non-vascular conditions, for instance in multi-drug resistance reversal, eg. in chemotherapy, and any other condition for which verapamil racemate may have utility.

As discussed above, (S)-verapamil has been suggested for the treatment of atrial fibrillation and angina. Accordingly, further embodiments of the present invention utilise (S)-verapamil for the treatment of patients suffering either from atrial fibrillation or angina, and who are disposed to constipation.

Administration of the single enantiomer may be by any of the conventional routes, for instance oral and sublingual. Conventional formulations may be used, including sustained-release formulations where appropriate. Typically, the single enantiomer will be formulated for oral administration. The dosage of the single enantiomer will typically depend upon the condition to be treated and/or the particular patient to be treated. Typically, however, the dosage will be lower than that usually used with the racemate, for instance up to 240 mg per day, and preferably not exceeding 200 mg per day. This is particularly true in the case of administration of (S)-verapamil for the treatment of angina, where side effects reported to be associated with this enantiomer may be particularly harmful at high dosages.

The data upon which the present invention is based are summarised below.

The effects of verapamil racemate and the individual enantiomers of verapamil on gastrointestinal transit were studied in 13 male volunteers in a four-way double blind cross-over study. All volunteers consumed a standard balanced diet throughout the period. In each phase of the study, each volunteer was assigned to one of four groups which received the following treatments, three times a day, over a period of 7 days.

Group A—120 mg racemic verapamil hydrochloride (a total of 360 mg drug per day).

Group B—60 mg (S)-verapamil hydrochloride (a total of 180 mg drug per day).

Group C—60 mg (R)-verapamil hydrochloride (a total of 960 mg drug per day).

Group D—320 mg Placebo (a total of 960 mg per day).

On day four of each study, the volunteers were also administered a capsule containing $^{111}$In labelled ion-exchange resin, to act as a marker of gastrointestinal transit. The minimum time interval between separate study periods was 7 days.

Statistical analysis of the large bowel transit data at 36 hours post dosing gave the following mean geometric centre readings for the four treatment groups: 3.79 (A), 4.43 (B), 4.53 (C), and 4.51 (D). The smaller the geometric centre reading, the slower the bowel transit. The mean geometric centre analysis utilised is described by Krevsky et al, Dig. Dis. Sci. (1992) 37: 919–924.

The results clearly demonstrate that at a daily dose of 360 mg racemic verapamil is capable of having a significant constipating effect on large bowel transit. No significant differences in large bowel transit were observed for either of the individual verapamil enantiomers or the placebo control. It is, therefore, believed that at a daily dose of 180 mg of either of the individual verapamil enantiomers no constipating effect should be observed, but that at the same time the same therapeutic benefit will be achieved, at half the dosage of the racemate.

We claim:

1. A method for treating a patient having a condition susceptible to treatment with racemic verapamil, wherein said method comprises administering to said patient an effective amount of a substantially single enantiomer of verapamil, either (R)-verapamil or (S)-verapamil, or a pharmaceutically-acceptable salt thereof, and wherein said patient is also disposed to constipation.

2. The method, according to claim 1, wherein said substantially single enantiomer of verapamil is (S)-verapamil.

3. The method, according to claim 1, wherein said substantially single enantiomer of verapamil is (R)-verapamil.

4. The method, according to claim 1, wherein said patient is cardiac-compromised.

5. The method, according to claim 1, wherein the condition is selected from the group consisting of atrial fibrillation, angina, hypertension, and paroxysmal supraventricular tachycarditis.

6. The method, according to claim 5, wherein said substantially single enantiomer is (S)-verapamil and said condition is atrial fibrillation.

7. The method, according to claim 5, wherein said substantially single enantiomer is (R)-verapamil and said condition is angina.

* * * * *